United States Patent
Li

(10) Patent No.: US 8,160,320 B2
(45) Date of Patent: Apr. 17, 2012

(54) MEDICAL IMAGE DISPLAY APPARATUS, METHOD AND PROGRAM, AND RECORDING MEDIUM FOR THE PROGRAM

(75) Inventor: Yuanzhong Li, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 950 days.

(21) Appl. No.: 12/170,947

(22) Filed: Jul. 10, 2008

(65) Prior Publication Data

US 2009/0016491 A1    Jan. 15, 2009

(30) Foreign Application Priority Data

Jul. 12, 2007   (JP) ................................. 2007-183418

(51) Int. Cl.
G06K 9/00 (2006.01)
(52) U.S. Cl. ...................................... 382/128
(58) Field of Classification Search .................. 382/128
See application file for complete search history.

(56) References Cited

U.S. PATENT DOCUMENTS

| | | | | |
|---|---|---|---|---|
| 6,771,263 B1 * | 8/2004 | Behrens et al. | ............... | 345/424 |
| 7,298,878 B2 * | 11/2007 | Goto | ............... | 382/128 |
| 7,556,602 B2 * | 7/2009 | Wang et al. | ............... | 600/437 |
| 7,597,663 B2 * | 10/2009 | Wang et al. | ............... | 600/437 |
| 7,828,732 B2 * | 11/2010 | Wang et al. | ............... | 600/437 |
| 2005/0251020 A1 | 11/2005 | Kondo et al. | | |

FOREIGN PATENT DOCUMENTS

| | | |
|---|---|---|
| JP | 06-292654 A | 10/1994 |
| JP | 11-055592 A | 2/1999 |
| JP | 11-306264 A | 11/1999 |
| JP | 2001-143095 A | 5/2001 |
| JP | 2002-143095 A | 5/2002 |
| JP | 2003-524489 A | 8/2003 |
| JP | 2004-180987 A | 7/2004 |
| JP | 2005-245011 A | 9/2005 |
| JP | 2005-334634 A | 12/2005 |
| JP | 2005-342128 A | 12/2005 |
| JP | 2006-014989 A | 1/2006 |
| JP | 2006-186434 A | 7/2006 |
| JP | 2006-197968 A | 8/2006 |

OTHER PUBLICATIONS

Decision of Rejection, dated Aug. 30, 2010, issued in corresponding JP Application No. 2007-183418, 6 pages in English and Japanese.
Japanese Office Action dated Apr. 7, 2010, corresponding to Application No. 2007-183418.
Tatsuro Hayashi et al., "Development of the Procedure for Automatic Extracting Interlobar Fissures and its Performance Evaluation", Technical Report of IEICE, Oct. 2003, pp. 39-44.

(Continued)

Primary Examiner — Dixomara Vargas
(74) Attorney, Agent, or Firm — Sughrue Mion, PLLC

(57) ABSTRACT

According to the medical image display apparatus of an aspect of the present invention, the display mode to provide multi-screen display of the plurality of slice images including the abnormal shadow region is determined based on the result of acquisition of the abnormal shadow region (three-dimensional information for the abnormal shadow region), which eliminates the necessity for users (doctors) to perform an operation to set a display mode, and enables display of the plurality of slice images including the abnormal shadow region efficiently in a display mode enabling easy image interpretation.

25 Claims, 14 Drawing Sheets

OTHER PUBLICATIONS

Y. Nakada et al., "A study on association of lung lobes to bronchial branches extracted from CT image", pp. 275-276, Nov. 2005.

Yoshito Mekada et al., "Automated Classification of Pulmonary Artery and Vein from Chest X-ray CT Images Based on Spatial Arrangement Features of Bronchus and Vessels", 2005, pp. 1412-1420, vol. J88-D-II, No. 8.

Chi-Ren Shyu et al., "ASSERT: A Physician-in-the-Loop Content-Based Retrieval System for HRCT Image Databases", Computer Vision and Image Understanding, Jul./Aug. 1999, pp. 111-132, vol. 75, No. 1/2.

Questioning, dated Feb. 21, 2011, issued in corresponding JP Application No. 2007-183418, 9 pages in English and Japanese.

English-language Abstract for Hayashi et al., "Development of the Procedure for Automatic Extracting Interlobar Fissures and its Performance Evaluation," originally filed in this application as part of the Information Disclosure Statement filed on Jul. 10, 2008.

English-language Abstract for JP 11-306264A, published Nov. 5, 1999, Applicant Toshiba Iyo System et al., orignally filed in this application as part of the Information Disclosure Statement filed on Jul. 7, 2010.

English-language Abstract for JP 2006-197968A, published Aug. 3, 2006, Applicant Toshiba Corp et al., originally filed in this application as part of the Information Disclosure Statement filed on Jul. 7, 2010.

English-language Abstract for Mekada et al., "Automated Clasification of Pulmonary Artery and Vein from Chest X-ray CT Image Based on Spatial Arrangement Features of Bronchus and Vessels," originally filed in this application as part of the Information Disclosure Statement filed on Jul. 10, 2008.

English-language Abstract for Nakada et al., "A study on association of lung lobes to bronchial branches extracted from CT image,"originally filed in this application as part of the Information Disclosure Statement filed on Jul. 10, 2008.

English-language Abstract of JP06-292654A, published Oct. 21, 1994, Applicant Fujitsu Ltd, originally in this application as part of the Information Disclosure Statemetn filed on Jul. 7, 2010.

Trial Decision, dated Aug. 24, 2011, issued in corresponding JP Application No. 2007-183418, 30 pages in English and Japanese.

* cited by examiner

FIG.9
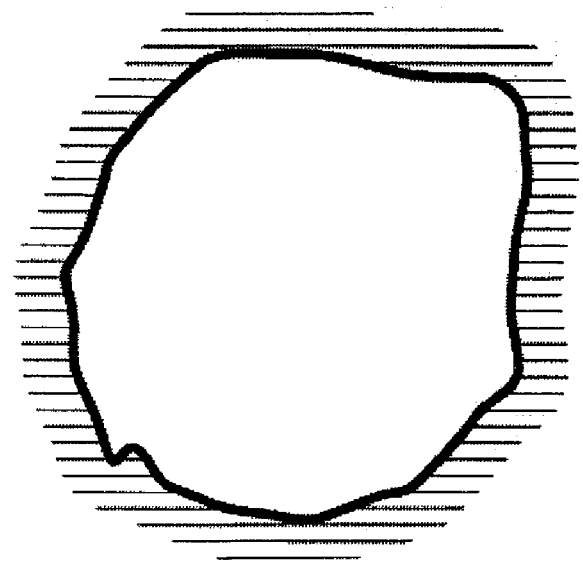
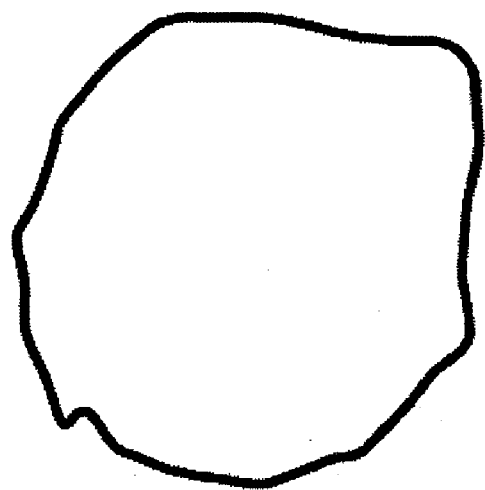

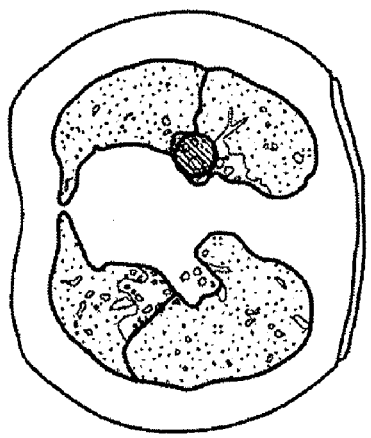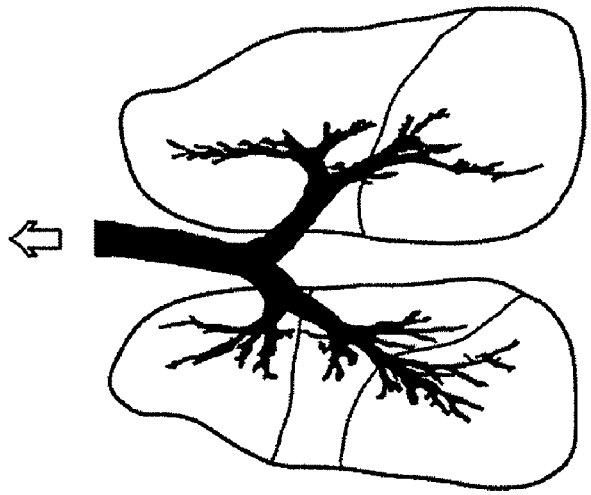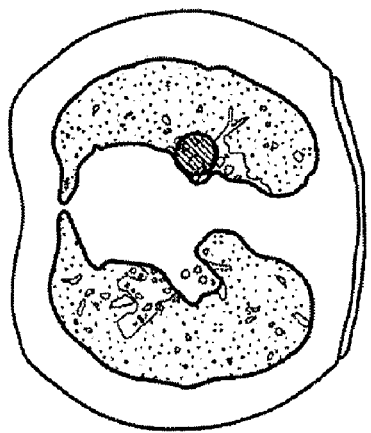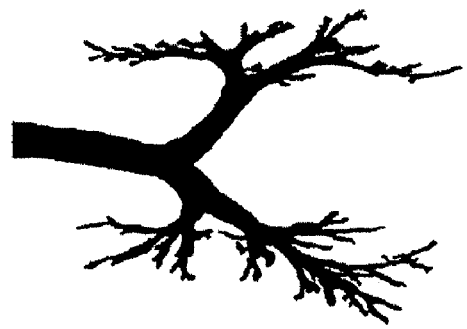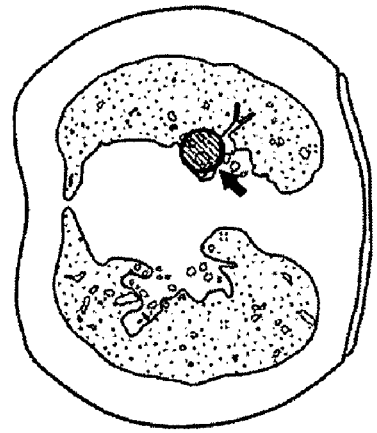

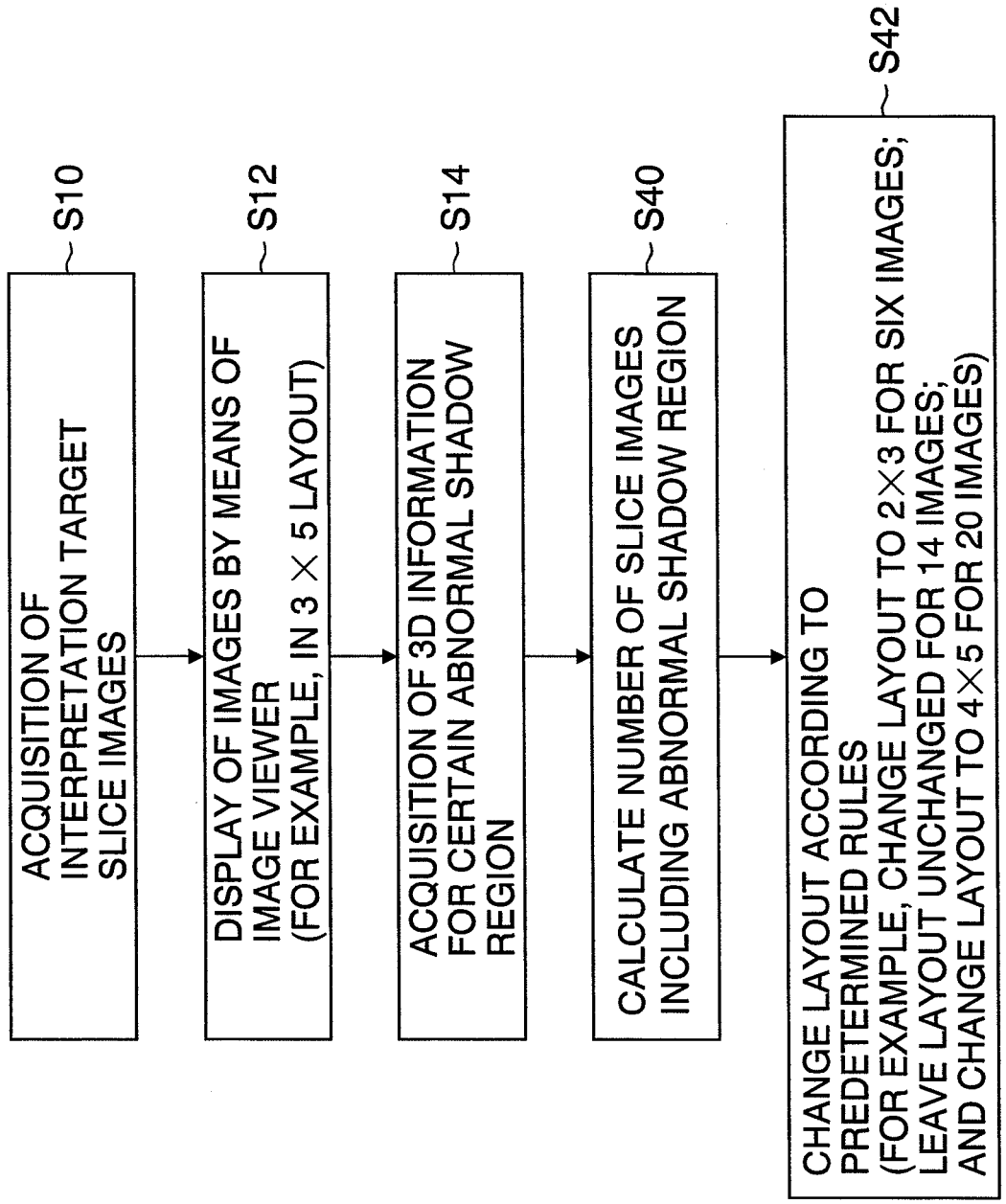

MEDICAL IMAGE DISPLAY APPARATUS, METHOD AND PROGRAM, AND RECORDING MEDIUM FOR THE PROGRAM

BACKGROUND OF THE INVENTION

1. Field of the Invention

The present invention relates to a medical image display apparatus, method and program, and recording medium for the program. More specifically, the present invention relates to a technique for displaying on a multi-screen a series of slice images taken by means of an X-ray CT apparatus or an MRI apparatus, etc.

2. Description of the Related Art

Conventionally, a medical image management and display system configured so that an image file containing medical images is provided with display mode information having information for a split screen and medical image frame positions, and when displaying the medical images contained in this image file on a viewer, the screen of the viewer is split according to the split screen information included in the display mode information, and the medical images are displayed at the corresponding positions in the split screen according to the frame position information included in the display mode information (Japanese Patent Application Laid-Open No. 2005-334634).

Here, "information for a split screen" refers to information for splitting one screen into a matrix of, for example, [2×2] or [3×3], and "information for frame positions" refers to information representing the positions of the respective display regions separated as a result of the screen splitting (for example, in the case of a split screen of [2×2], it is information representing (1, 1), (1, 2), (2, 1) and (2, 2). Also, the aforementioned display mode information can arbitrarily be input by users.

Also, Japanese Patent Application Laid-Open No. 2002-143095 describes a medical image display system that displays medical images on a display screen according to display conditions such as the number of screen segments and the layout of images. In the medical image display system, for example, when a doctor wishes to make CT images display with a display screen split into nine segments, if the actually displayed screen is not the display conditions the doctor wishes, such as the case where split into four segments, the doctor re-sets the display mode to a desired one in the image display apparatus and re-display the images.

SUMMARY OF THE INVENTION

However, the medical image management and display system described in Patent Document 1 has a problem in that it requires a user to provide display mode information to each medical image in advance, which is cumbersome.

Also, the medical image display system described in Patent Document 2 requires a doctor to set display conditions such as the number of screen segments and the layout of images when displaying a plurality of CT images on a multi-screen.

Furthermore, in recent years, since numerous slice images are taken at one time by means of a multi-slice X-ray CT apparatus or the like, efficient image interpretation is needed, but the inventions described in Japanese Patent Application Laid-Open No. 2005-334634 and Patent Application Laid-Open No. 2002-143095 cannot meet that need.

The present invention has been made in view of these circumstances, and an object of the present invention is to provide a medical image display apparatus, method and program, and recording medium for the program which can display a plurality of slice images including an abnormal shadow region from a series of slice images constituting a three-dimensional medical image in a mode that is efficient and enables easy image interpretation, thereby contributing to improving the efficiency of image interpretation.

In order to achieve the above object, a medical image display apparatus according to a first aspect of the present invention comprises: an acquisition device which acquires a series of slice images constituting a three-dimensional medical image that is a diagnosis target; an abnormal shadow region acquisition device which acquires three-dimensional information for an abnormal shadow region included in the acquired series of slice images; a determination device which determines a display mode to provide multi-screen display of a plurality of slice images including the abnormal shadow region from the series of slice images based on the acquired three-dimensional information for the abnormal shadow region; a display screen creation device which creates a display screen for providing multi-screen display of the plurality of slice images including the abnormal shadow region based on the plurality of slice images including the abnormal shadow region and information for the determined display mode; and an output device which outputs the created display screen to a display device.

The display mode to provide multi-screen display of the plurality of slice images including the abnormal shadow region is determined based on the result of acquisition of the abnormal shadow region (three-dimensional information for the abnormal shadow region), which eliminates the necessity for users (doctors) to perform an operation to set a display mode, and enables display of the plurality of slice images including the abnormal shadow region efficiently in a display mode enabling easy image interpretation.

Here, the information for the display mode includes information specifying a split screen type from a plurality of split screen types that are different from each other in the number of screen segments, and information representing the layout of the plurality of slice images including the abnormal shadow region on the split screen, and the determination device at least determines the layout of the plurality of slice images including the abnormal shadow region.

Also, it is possible to obtain, for example, the slicing positions for the plurality of slice images including the image of the abnormal shadow region from the series of slice images, the area of the abnormal shadow region in each slice image, and the length in the slicing-proceeding direction of the abnormal shadow region, based on the three-dimension information for the abnormal shadow region. Examples of the abnormal shadow region include candidate regions for brain tumor, chest node, liver tumor, liver cyst, kidney cyst, etc.

A second aspect of the present invention provides the medical image display apparatus according to the first aspect, wherein the abnormal shadow region acquisition device includes: an extraction device which automatically extracts the abnormal shadow region included in the respective sliced images by analyzing the acquired series of slice images; and an outer shape information acquisition device which acquires three-dimensional information representing the outer shape of the extracted abnormal shadow region.

A third aspect of the present invention provides the medical image display apparatus according to the first aspect, wherein the abnormal shadow region acquisition device includes: a display device which displays at least one slice image from the acquired series of slice images; a designation device which designates a seed point in the abnormal shadow region in the slice image displayed on the display device; an extraction device which extracts the abnormal shadow region with reference to the designated seed point; and an outer shape information acquisition device which acquires three-dimensional information for an outer shape of the extracted abnormal shadow region.

A fourth aspect of the present invention provides the medical image display apparatus according to the second or third aspect, further comprising a recording device which records, in a recording medium, the three-dimensional information representing the outer shape of the abnormal shadow region acquired by the outer shape information acquisition device in association with the series of slice images, wherein the abnormal shadow region acquisition device acquires three-dimensional information for the abnormal shadow region by reading the three-dimensional information representing the outer shape of the abnormal shadow region recorded in the recording medium. As a result, it is possible to use the recorded extraction result at a subsequent image interpretation.

A fifth aspect of the present invention provides the medical image display apparatus according to any of the first to fourth aspects, wherein: the information for the display mode includes information for specifying a split screen type from a plurality of split screen types having different numbers of screen segments, and information representing layout of the plurality of slice images including the abnormal shadow region on the split screen; and the determination device calculates the number of the plurality of slice images including the abnormal shadow region based on the acquired three-dimensional information for the abnormal shadow region, and determines, based on the calculated number of slice images, a split screen having the number of screen segments corresponding to the number of slice images.

For example, a determination is made to use a split screen having the smallest number of screen segments in split screens each having the number of screen segment that is equal to or exceeds the number of slice images in which the image of the abnormal shadow region is successively present. Consequently, the plurality of slice images including the abnormal shadow region can be displayed on one screen.

Also, if there is a large number of slice images in which the abnormal shadow region is successively present, it becomes impossible to lay out all the images of the abnormal shadow region on one screen. In that case, a determination is made to use a split screen having the largest number of screen segments.

A sixth aspect of the present invention provides the medical image display apparatus according to any of the first to fifth aspects, wherein the information for the display mode includes information for specifying a split screen type from a plurality of split screen types having different numbers of screen segments, and information representing layout of the plurality of slice images including the abnormal shadow region on the split screen; and the determination device determines the layout of the plurality of slice images including the abnormal shadow region on the split screen so that a slice image having a largest area of the abnormal shadow region in the plurality of slice images including the abnormal shadow region is arranged in the center of the display screen.

As a result, the slice image that should be most noted can be displayed at a prominent position on the display screen (the center of the screen).

A seventh aspect of the present invention provides the medical image display apparatus according to any of the first to fifth aspects, wherein: the information for the display mode includes information for specifying a split screen type from a plurality of split screen types having different numbers of screen segments, and information representing layout of the plurality of slice images including the abnormal shadow region on the split screen; and the determination device determines the layout of the plurality of slice images including the abnormal shadow region on the split screen so that a slice image at a center position in the plurality of slice images including the abnormal shadow region is arranged in a center of the display screen.

An eighth aspect of the present invention provides the medical image display apparatus according to any of the first to fifth aspects, wherein the information for the display mode includes information for specifying a split screen type from a plurality of split screen types having different numbers of screen segments, and information representing layout of the plurality of slice images including the abnormal shadow region on the split screen; and the determination device determines the layout of the plurality of slice images including the abnormal shadow region on the split screen so that a first slice image in the plurality of slice images including the abnormal shadow region is arranged in a corner of the display screen.

A medical image display method according to a ninth aspect of the present invention comprises the steps of: acquiring a series of slice images constituting a three-dimensional medical image that is a diagnosis target; acquiring three-dimensional information for an abnormal shadow region included in the acquired series of slice images; determining a display mode to provide multi-screen display of a plurality of slice images including the abnormal shadow region from the series of slice images based on the acquired three-dimensional information for the abnormal shadow region; creating a display screen for providing multi-screen display of the plurality of slice images including the abnormal shadow region based on the plurality of slice images including the abnormal shadow region and information for the determined display mode; and outputting the created display screen to a display device.

A medical image display program according to a tenth aspect of the present invention causing a computer to execute: a function which acquires a series of slice images constituting a three-dimensional medical image that is a diagnosis target; a function which acquires three-dimensional information for an abnormal shadow region included in the acquired series of slice images; a function which determines a display mode to provide multi-screen display of a plurality of slice images including the abnormal shadow region from the series of slice images based on the acquired three-dimensional information for the abnormal shadow region; a function which creates a display screen for providing multi-screen display of the plurality of slice images including the abnormal shadow region based on the plurality of slice images including the abnormal shadow region and information for the determined display mode; and a function which outputs the created display screen to a display device.

In order to achieve the above object, an eleventh aspect of the present invention provides a recording medium in which computer readable code of the medical image display program according to the tenth aspect is stored.

According to the present invention, it is possible to automatically display a plurality of slice images including an abnormal shadow region from a series of slice images constituting a three-dimensional medical image in a display mode that is efficient and enables easy image interpretation, thereby enabling contributing to the improvement of the efficiency of image interpretation.

BRIEF DESCRIPTION OF THE DRAWINGS

FIG. 9 is a diagram illustrating an attention region and its surrounding area;

FIGS. 10A to 10E are diagrams used for describing a method for analyzing the anatomical position of a chest image;

FIG. 14 is a flowchart illustrating a fourth embodiment of a medical image display method according to the present invention.

DETAILED DESCRIPTION OF THE PREFERRED EMBODIMENTS

Hereinafter, preferred embodiments of a medical image display apparatus, method and program, and recording medium for the program according to the present invention will be described with reference to the attached drawings.

<System Configuration>

Figure 1:
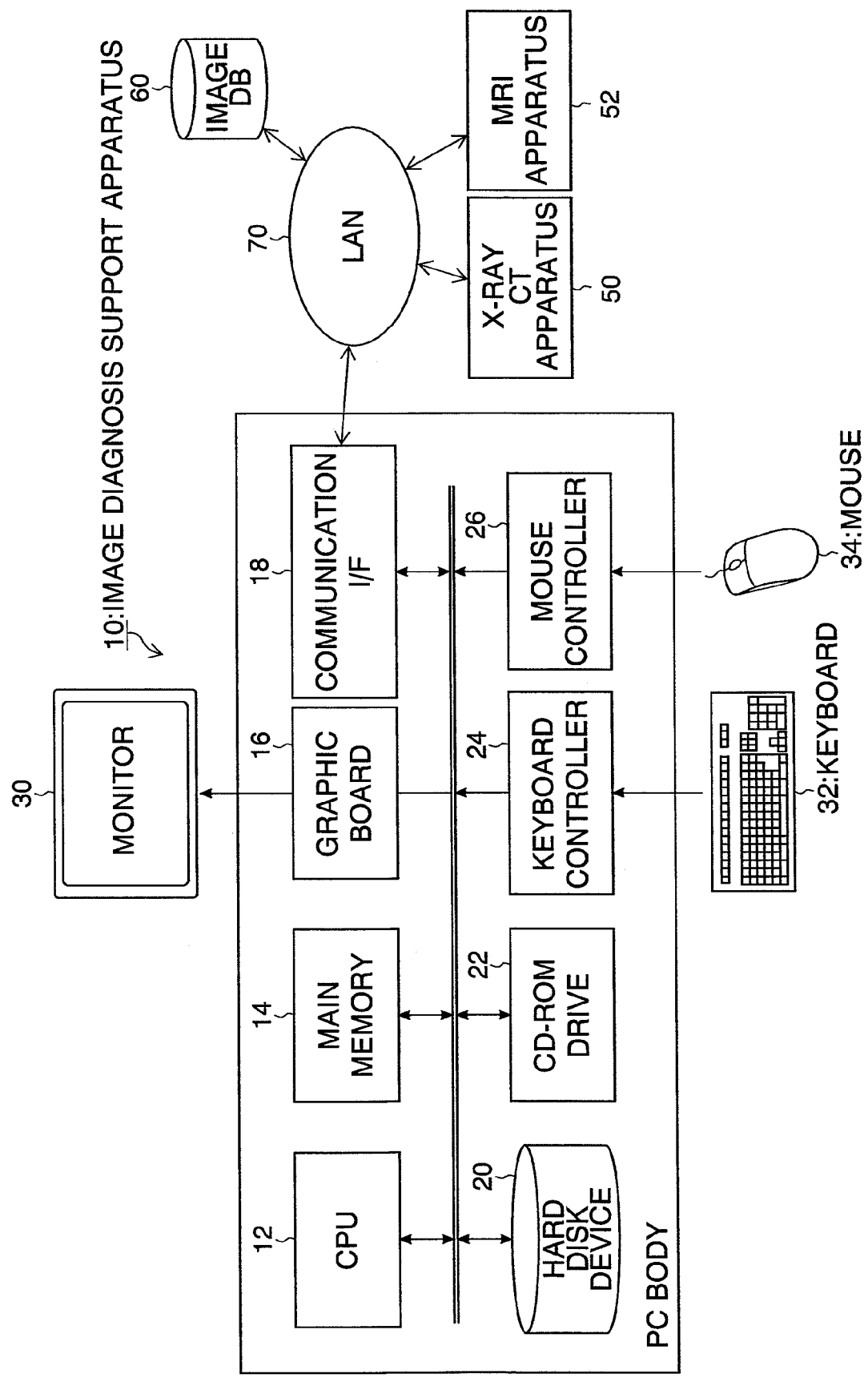
FIG. 1 is a system configuration diagram of a medical image management system, such as a PACS (Picture Archiving and Communication System), that includes a medical image display apparatus according to the present invention.

FIG. 1 is a system configuration diagram of a medical image management system, such as a PACS, that includes a medical image display apparatus according to the present invention.

This medical image management system mainly includes a medical image display apparatus 10, which is operated by diagnostic radiologists, clinicians, etc., an X-ray CT apparatus 50, an MRI apparatus 52, image database (image DB) 60, and a network 70, such as an in-house LAN, that connects these devices.

The medical image display apparatus 10, which is constituted by a personal computer (PC), mainly includes a central processing unit (CPU) 12 that controls the operation of the respective components, main memory 14 that stores a control program for the apparatus and becomes a work area at the time of the program being executed, a liquid-crystal display, a graphic board 16 that controls the display on a monitor device 30 such as a CRT display, a communication interface (communication I/F) 18 connected to the network 70, an operating system (OS) for the PC, device drivers for peripheral devices connected to the PC, a hard disk device 20 in which various application software, etc., including a medical image display program according to the present invention, are stored, a CD-ROM drive 22, a keyboard controller 24 that detects a key operation in a keyboard 32 and outputs it to the CPU 12 as an input of an instruction, and a mouse controller 26 that detects the state of a mouse 34, which is a positional input device, and outputs signals, such as those for the position of a mouse pointer in the monitor device 30 and the state of the mouse 34, to the CPU 12.

Incidentally, the recording medium according to the present invention can be provided as a recording medium such as a hard disk device, a compact disk, and a DVD disk, etc. in which the medical image display program according to the present invention is stored.

Since the PC having the aforementioned configuration is known except the medical image display program according to the present invention stored in the hard disk device 20, the detailed description of the respective components is omitted.

Figure 2:
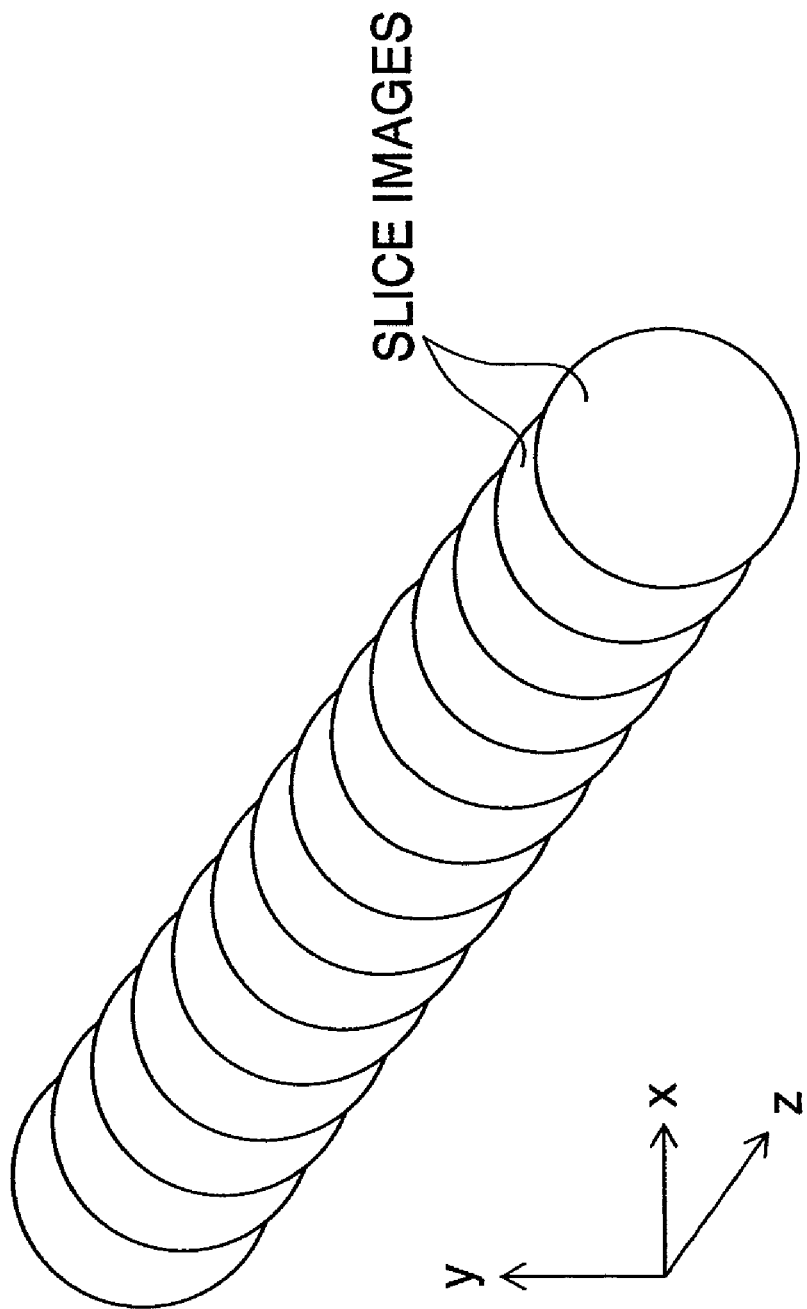
FIG. 2 is a diagram used for describing a series of slice images.

The X-ray CT apparatus 50 and the MRI apparatus 52, as shown in FIG. 2, each take multiple successive images along the z-axis direction (the body-axis direction of a subject). A series of slice images taken by the X-ray CT apparatus 50 and the MRI apparatus 52 at one time is stored in the image DB 60.

The image DB 60 associates the series of slice images with modality kinds such as patient, image-taking data and time, body part of which the images have been taken, and the X-ray CT apparatus 50 or the MRI apparatus 52, and stores and manages the series of slice images by means of the modalities.

A diagnostic radiologist or clinician operates the medical image display apparatus 10 to acquire the series of slice images from the image DB 60 via the network 70, and as described later, makes, for example, slice images including an image of an abnormal shadow region be displayed on the monitor device 30, and interprets the images displayed on the monitor device 30 to prepare an image interpretation report or medical records.

<Medical Image Display Apparatus>

Figure 3:
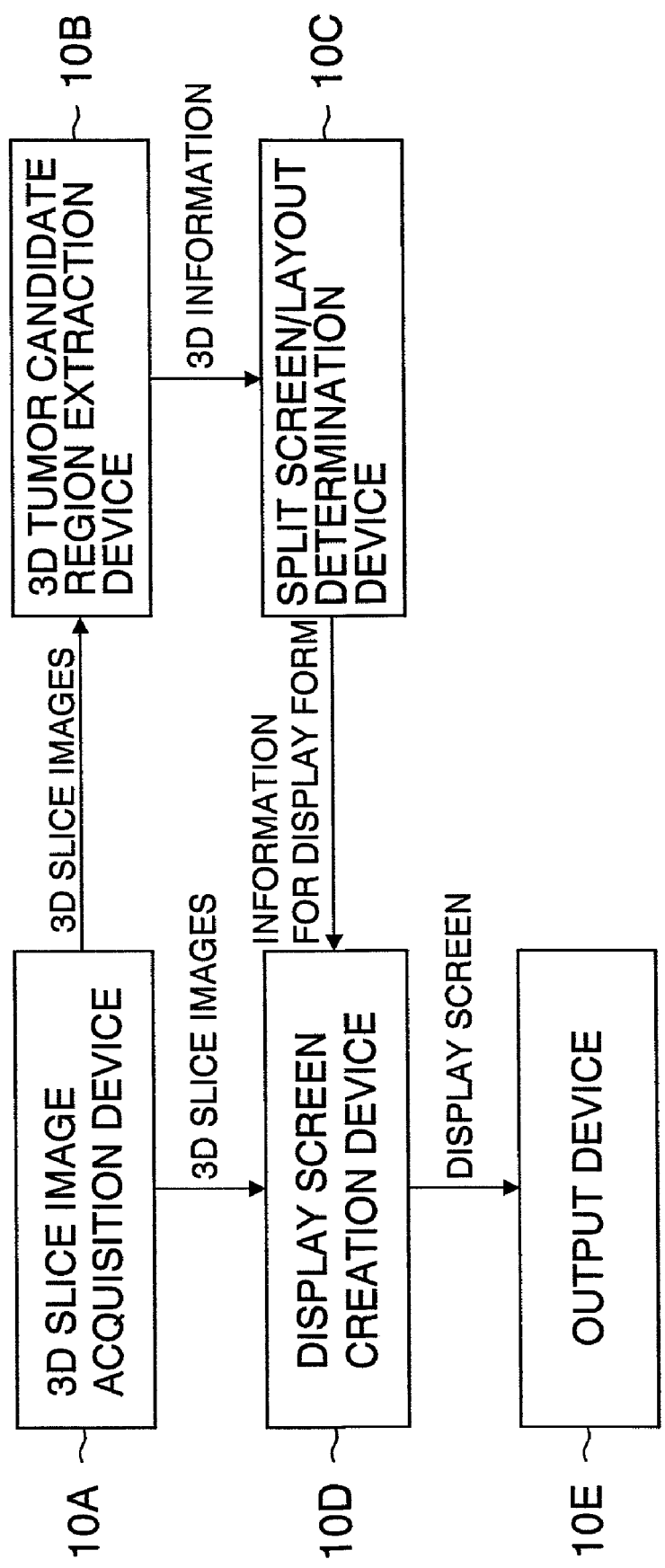
FIG. 3 is a functional block diagram illustrating the functions of the medical image display apparatus shown in FIG. 1.

FIG. 3 is a functional block diagram illustrating the functions of the medical image display apparatus 10 having the aforementioned configuration.

The medical image display apparatus 10 includes a 3D slice image acquisition device 10A, a 3D tumor candidate region extraction device 10B, split screen/layout determination device 10C, a display screen creation device 10D, and an output device 10E.

The 3D slice image acquisition device 10A acquires a series of slice images constituting a three-dimensional (3D) medical image from the image DB 60 via the network 70.

The 3D tumor candidate region extraction device 10B extracts an abnormal shadow region (3D tumor candidate region) included in the acquired series of slice images to acquire 3D information representing the outer shape of this extracted 3D tumor candidate region. Examples of 3D information representing the outer shape of 3D tumor candidate region may include the 2D coordinates (x-y coordinates) for the contour points of the image of the 3D tumor candidate region in each slice image, and the slicing positions (z coordinates) for the slice images including the image of the 3D tumor candidate region. From this 3D information representing the outer shape of the 3D tumor candidate region, the slicing positions for a plurality of images including the image of the 3D tumor candidate region from the series of slice images, the area of the 3D tumor candidate region in each slice image, and the length in the slicing-proceeding direction of the 3D tumor candidate region, etc, can be obtained. The details of a method for extracting a 3D tumor candidate region by means of the tumor candidate region extraction device 10B will be described later.

The split screen/layout determination device 10C determines the display mode (split screen/layout) to provide multi-screen display of the plurality of slice images including the 3D tumor candidate region from the series of slice images based on the 3D information for the 3D tumor candidate region extracted by the tumor candidate region extraction device 10B, and for example, it determines the split screen type such as a six-split screen with a 2×3 matrix, a 15-split screen with a 3×5 matrix or a 20-split screen with a 4×5 matrix, or determines the layout of the plurality of slice images including the 3D tumor candidate region on the determined split screen. The split screen type or the number of screen segments may be set by a user.

The display screen creation device 10D creates a display screen for multi-screen display in which the plurality of slice images including the image of the 3D tumor candidate region from the 3D slice images are laid out on a split screen, based on the information for the display mode determined by the split screen/layout determination device 10C.

The output device 10E outputs the display screen created by the display screen creation device 10D to the monitor device 30.

<First Embodiment>

Figure 4:
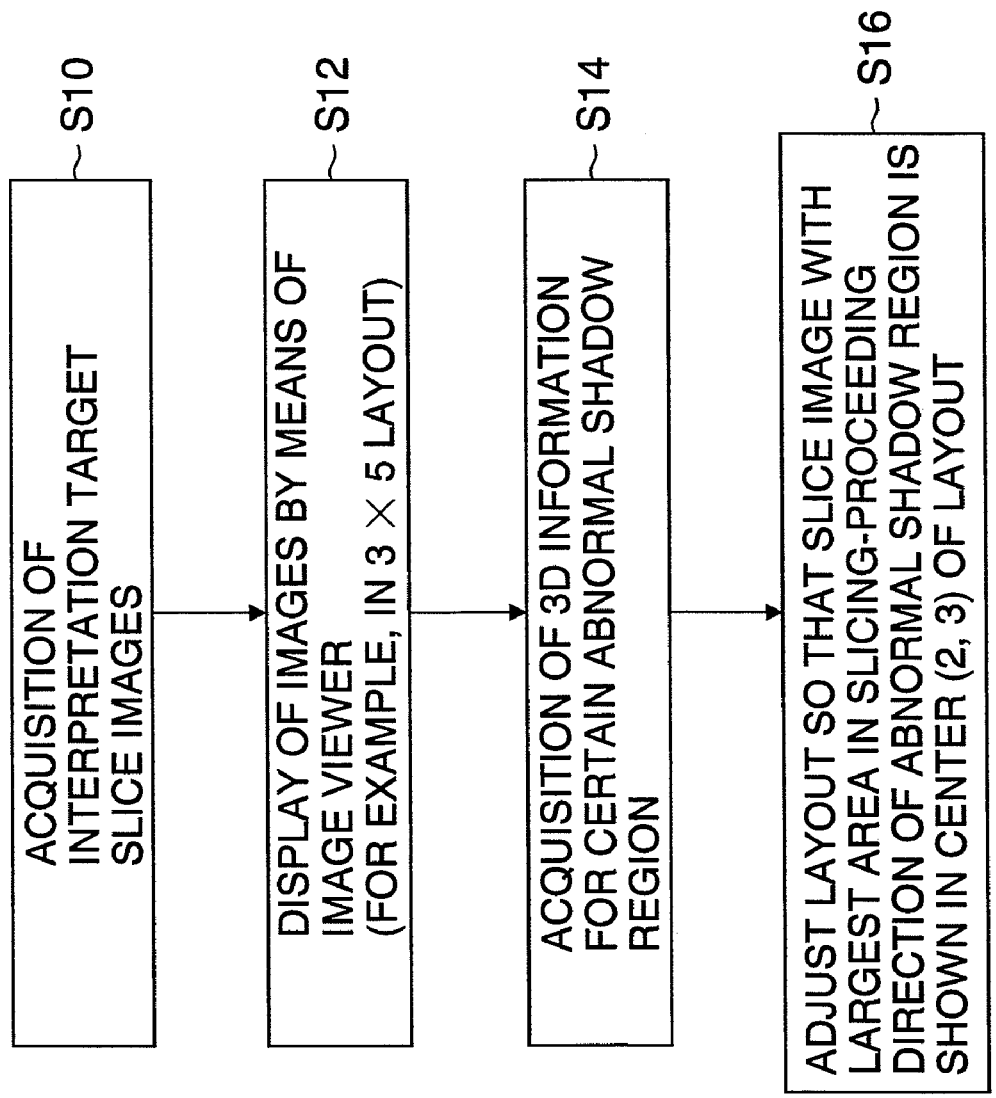
FIG. 4 is a flowchart illustrating a first embodiment of a medical image display method according to the present invention.

FIG. 4 is a flowchart illustrating a first embodiment of a medical image display method according to the present invention, and this processing is executed by starting a medical image display program.

A diagnostic radiologist operates the keyboard 32 and/or the mouse 34 of the medical image display apparatus 10 to input a patient's name, a date and time of the image-taking, a body part of which the images were taken and a 3D modality type, etc., and acquires a group of slice images (a series of slice images), which is the interpretation target, from the image DB 60 based on this input information (step S10).

Subsequently, multi-screen display of a plurality of slice images from the acquired series of slice images is provided on the monitor device 30 (step S12). Here, when a 15-split screen in which one screen is split into 3×5 segments is set as a split screen for multi-screen display of the plurality of slice images, 15 slice images, i.e., the first to fifteenth slice images from the series of slice images are displayed in such a manner that they are arranged from the upper left corner (1, 1) to the lower right corner (3, 5) of the 15-split screen in the order of their slicing positions.

Next, the medical image display apparatus 10 semiautomatically or automatically acquires three-dimensional information (3D information) representing the outer shape of a certain abnormal shadow region (3D tumor candidate region) from the acquired series of slice images, by means of the medical image display program's image analysis (step S14).

Here, an extraction method for semiautomatically extracting an abnormal shadow region will be described.

First, a diagnostic radiologist performs diagnostic imaging while providing an instruction to change a plurality of slice images to be displayed on the monitor device 30 (for example, an instruction to switch multi-screens by turning the mouse wheel forward or backward or operating up and down keys on the keyboard 32, etc., or an instruction to scroll the slice images) via the keyboard 32 or the mouse 34, and select a desired slice image (for example, a slice image including a relatively large area of the abnormal shadow region).

Figure 5:
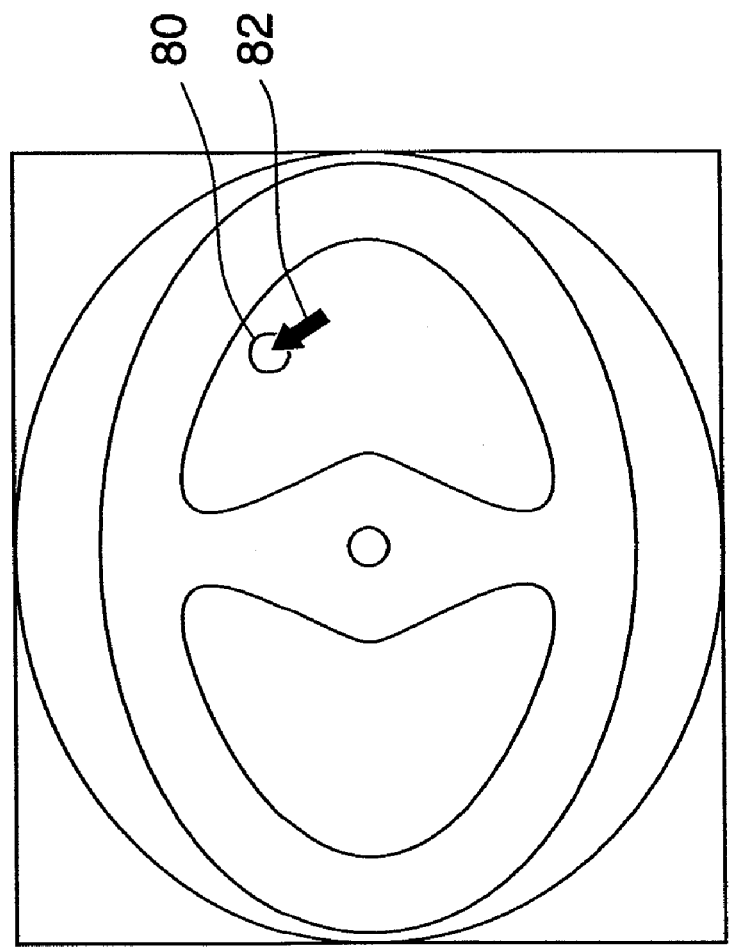
FIG. 5 is a diagram used for describing the designation of a seed point when semiautomatically extracting an abnormal shadow region.

Subsequently, as shown in FIG. 5, the diagnostic radiologist moves a cursor 82 via the mouse to the center (seed point) of an abnormal shadow region 80 in the slice image displayed on the monitor device 30, and marks it by means of one-click 3D measurement to execute semiautomatic extraction of the abnormal shadow region.

The one-click 3D measurement of the abnormal shadow region is performed in such a manner described below.

Figure 6D:
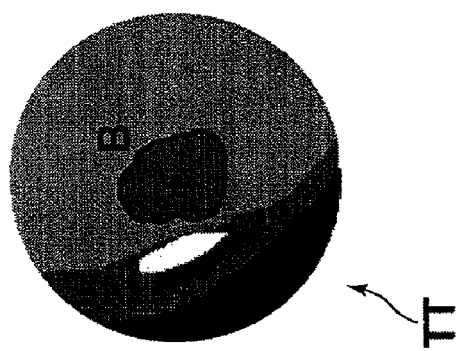
FIGS. 6A to 6D are diagrams used for describing a method for automatic extraction of an abnormal shadow region.
Figure 6C:
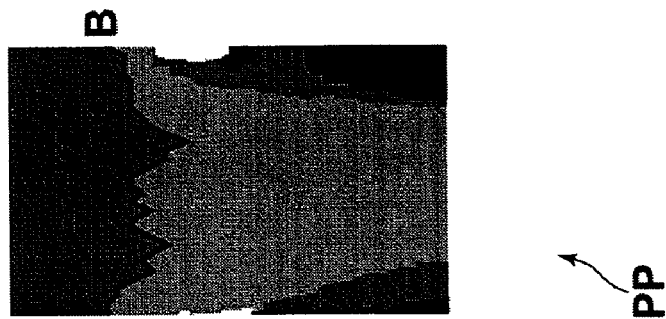
Figure 6B:
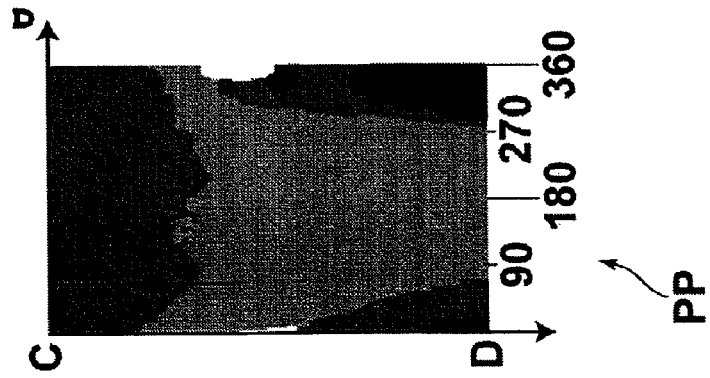
Figure 6A:
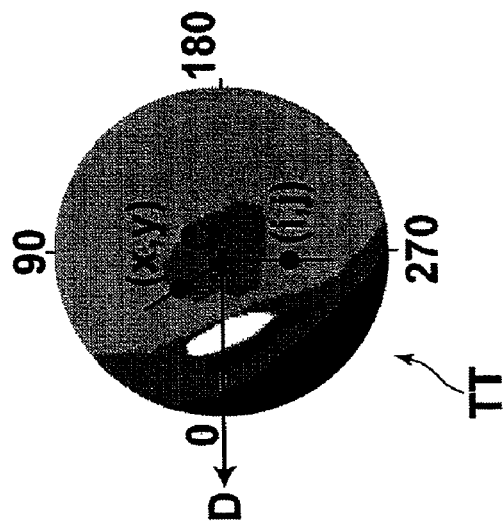

First, as shown in FIG. 6A, an abnormal shadow region (tumor candidate region) with a designated point C as its center is extracted. It is desirable to designate a point close to the center of the tumor candidate region as this point C.

A region with a fixed diameter sufficiently including the tumor candidate region is determined as a discrimination region TT.

Next, an image of the discrimination region TT as shown in FIG. 6A is transformed into a discrimination image PP plotted in a polar coordinate plane represented by the distance from the point C and angle θ formed with a predetermined straight line passing through the point C. For example, whether or not each pixel in the discrimination region is a contour of the tumor candidate region is determined using a polar coordinate image shown in FIG. 6B obtained by performing polar coordinate transformation of the image shown in FIG. 6A with the clockwise direction with reference to the line segment C-D in the radial direction of the image shown in FIG. 6A as angle θ.

Based on the feature quantity extracted from luminance information in a one-dimensional luminance profile for a straight line passing through each pixel (x, y) in the discrimination region and the point C, an evaluation value to determine whether or not each pixel (x, y) in the discrimination region is a pixel representing a contour is calculated.

In the one-dimensional luminance profile for a straight line passing through each pixel (x, y) and the point C, the luminance value rapidly changes for the part around the contour of the tumor candidate region. Accordingly, the feature quantities are calculated from the luminance values and a discriminator using these feature quantities is created. Based on the result obtained by the discriminator, an image (x, y) constituting a contour such as that expressed by a bold line B in FIG. 6C is obtained. Then, the discrimination region PP expressed in a polar coordinate system is inversely transformed into an ordinary coordinate system to determine the contour of the discrimination region TT in the image as shown in FIG. 6D. The region surrounded by this contour is extracted as a tumor candidate region (i.e., abnormal shadow region).

Alternatively, an abnormal shadow region may be extracted using a region separation technique described, for example, in "Volu-metric measurements of pulmonary nodules at multi-row detector CT: in vivo reproducibility" by Womanns D., Kohl G., Klotz E., et al. Eur Radiol 2004; 14(1): 86-92.

The 3D information representing the outer shape of the abnormal shadow region is acquired by performing the aforementioned abnormal shadow region extraction with regard to the successive slice images.

Also, when an abnormal shadow region is automatically extracted, the slice images are analyzed to analyze the features of an attention region.

If the attention region is an abnormal shadow such as a tumor or a pulmonary nodule appearing in a lung field, it exhibits some features in shape, size, and/or densities in the edge portion and in the region. Also, the anatomical position at which each abnormal shadow appears can also be considered as a feature of that abnormal shadow. Accordingly, the attention region is analyzed to obtain the features in shape, size, densities in the attention region and the edge portion of the attention region, and the anatomical position, etc.

(1) Shape Features

Figure 7:
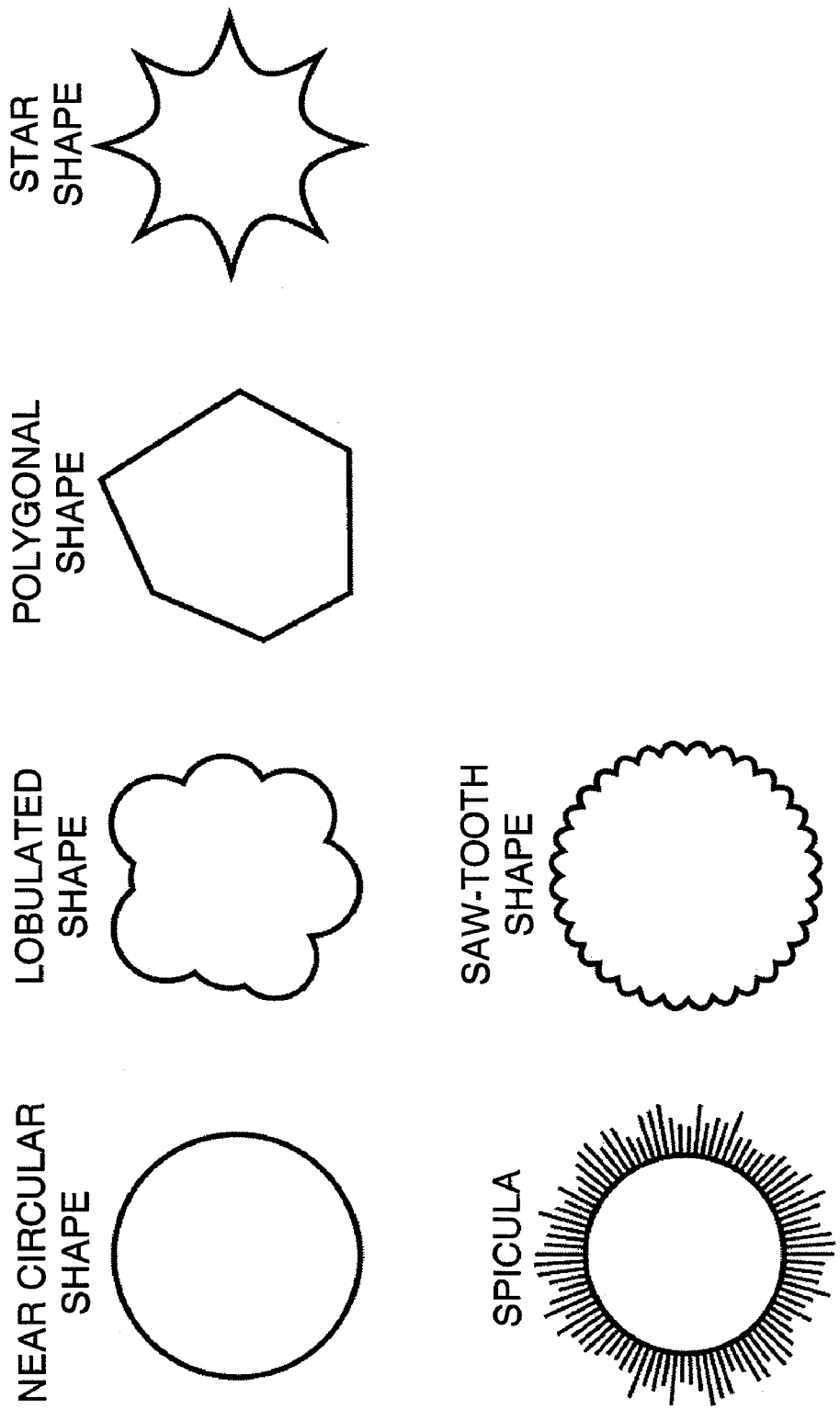
FIG. 7 is a diagram illustrating examples of abnormal shadow region shape classification.

The shapes of abnormal shadows can be classified into near circular shape, lobulated shape, polygonal shape, star shape, spicula, saw-tooth shape and irregular shape, as shown in FIG. 7 (For details, see, for example, "Computer-aided diagnosis for determining benign or malignant solitary pulmonary nodule" by Iwano et al., JRC2006).

These shapes can be classified using the degree of circularity (the ratio between the perimeter and the area), and a secondary gravity center moment (the total sum of squares of the distances between the gravity center of a nodule and the respective pixel points in the nodule, normalized by the square of the area).

Figure 8:
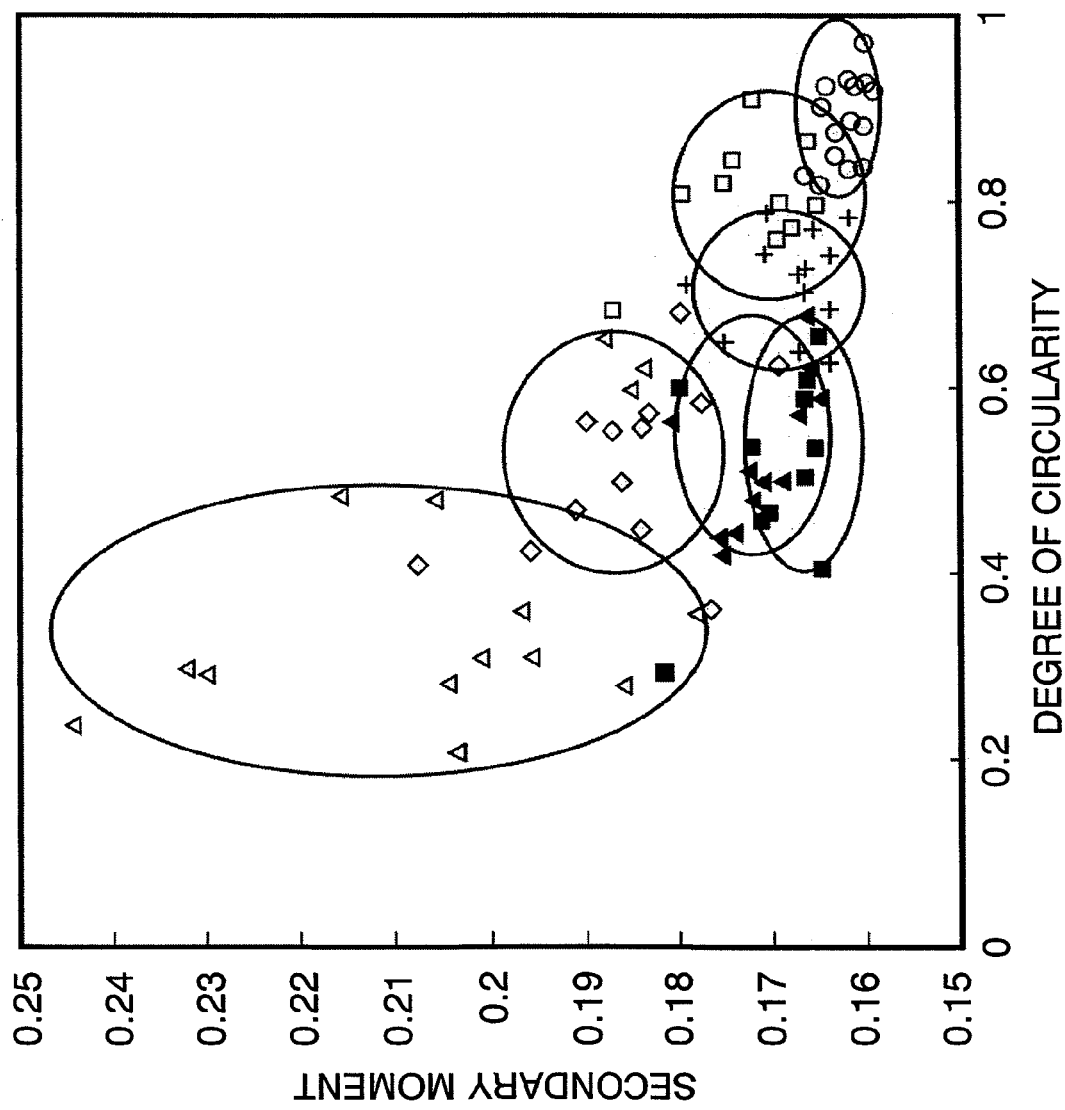
FIG. 8 is a diagram indicating the relationship between the abnormal shadow region shape classification, the secondary moment, and the degree of circularity.

The degree of circularity and the secondary moment exhibit distributions as shown in FIG. 8, which are classified into near circular shape, lobulated shape, polygonal shape, star shape, specula, saw-tooth shape and irregular shape (shape not belonging to any of the foregoing types) in their respective areas encircled by ellipsoids. Therefore, a discriminator that outputs a shape type upon the input of feature quantities such as degree of circularity and secondary moment can be provided using an existing non-linear discrimination technique or a design discrimination technique, etc.

(2) Size Features

The size of an abnormal shadow is represented by area, volume, long axis and short axis lengths, and can automatically be measured from the extracted attention region.

(3) Density Features Within the Attention Region

Abnormal shadows are classified into pure GGO (ground glass opacity), mixed GGO (ground glass opacity and high density), solid (high density) depending on the density. The discrimination can be made using the average value, the deviation, the maximum value and the minimum value within the attention region extracted by means of the aforementioned extraction device 43 as feature quantities, and also using an existing non-linear discrimination technique, a design discrimination technique, etc.

Furthermore, from the density values, abnormal shadows can be classified depending on whether or not any calcification or cavity is included in the region of the abnormal shadow. If the maximum density value of an attention region is equal to or greater than a certain threshold value (e.g., a rough standard CT value of 500), the attention region is determined to include calcification. If the minimum density value of an attention region is no more than a certain threshold value (e.g., a round standard CT value of 500), the attention region is determined to include a cavity.

(4) Density Features in Edge Portion of Attention Region

Abnormal region edge portions can be classified into well-defined ones and poorly-defined ones. Whether an edge portion is well-defined or poorly-defined is determined using the difference in density between the outside and the inside of the contour of the attention region extracted by means of an analysis program 14. The density difference is calculated from the density value of the inner area of the attention region with the bold line shown in FIG. 9 as its contour (the inside of the contour) and the density value of the surrounding area (the shaded area outside the contour) according to the following formula.

Density Difference=[average density value (surrounding area)−average density value (inner area)]/ [variance (surrounding area)+variance (inner area)]

(5) Anatomical Position

Next, the anatomical position of the attention region is recognized. For example, in an image of a chest, as shown in FIGS. 10A to 10E, first, the lung fields (see FIG. 10B) and the bronchial tubes (see FIG. 10D) are automatically extracted from the input chest image (see FIG. 10A). Furthermore, the interlobar fissures are extracted based on the shape of the bronchial tubes (see FIGS. 10C and 10E), classification of the lung lobes (in which the lung fields are classified) (into right upper, intermediate and lower lobes, and left upper and lower lobes) (For details, see Literature 1 "Development of the Procedure for Automatic Extracting Interlobar Fissures and its Performance Evaluation" by Tatsuro Hayashi, Zhou Xiangrong, Takeshi Hara, Hiroshi Fujita, Ryujiro Yokoyama, Takuji Kiryu and Hiroaki Hoshi, Technical Report by Institute of Electronics, Information and Communication Engineers (IEICE), MI2003-53, 39-44 (2003), Literature 2, "Study on Classification of Lobe Bronchi Extracted from Three-Dimensional Breast CT Image" (Nakata, et al., Fifteenth Conference of Japan Society of Computer Aided Diagnosis of Medical Images, p. p. 275-276, 2005.11), Literature 3, "Automated Classification of Pulmonary Artery and Vein from Chest X-ray CT Images Based on Spatial Arrangement Features of Bronchus and Vessels" by Tanaka et al., IEICE Transactions, DII, Vol. J88, p.p. 1421-1431, 2005.4, and Literature 4, "A Physician-in-the-loop Content-Based Image Retrieval System for HRCT Image Databases" by Shyu C., Brodley C. E., Kak A., Kosaka A., Aisen A., Broderick L., ASSERT, Computer Vision and Image Understanding, 1999; 74: 111-132, etc.). For example, the anatomical position of the attention region shown in FIG. 10A (the part indicated by the black arrow) is recognized as "left lung, upper lobe, S2".

By means of obtaining the feature quantities for an attention region in a slice image in a manner described above, whether or not the attention region is an abnormal shadow region is determined, and then by means of extracting an abnormal shadow region with regard to successive slice images in a manner described above, 3D information representing the outer shape of the abnormal shadow region (3D tumor candidate region) is acquired.

Referring back to FIG. 4, after the acquisition of 3D information representing the outer shape of the abnormal shadow region, a slice image having the largest area of the abnormal shadow region in the plurality of slice images including the abnormal shadow region is obtained by means of the medical image display program. Since the contour of the abnormal shadow region (3D information) is obtained for each slice image, the area of the abnormal shadow region included in each slice image can be obtained by calculating the number of pixels within the contour.

Then, with reference to the slice image having the largest area of the region, the layout of the plurality of slice images including the abnormal shadow region on the split screen is determined, and a display screen for providing multi-screen display of the plurality of slice images including the abnormal shadow region is created (step S16).

Figure 11:
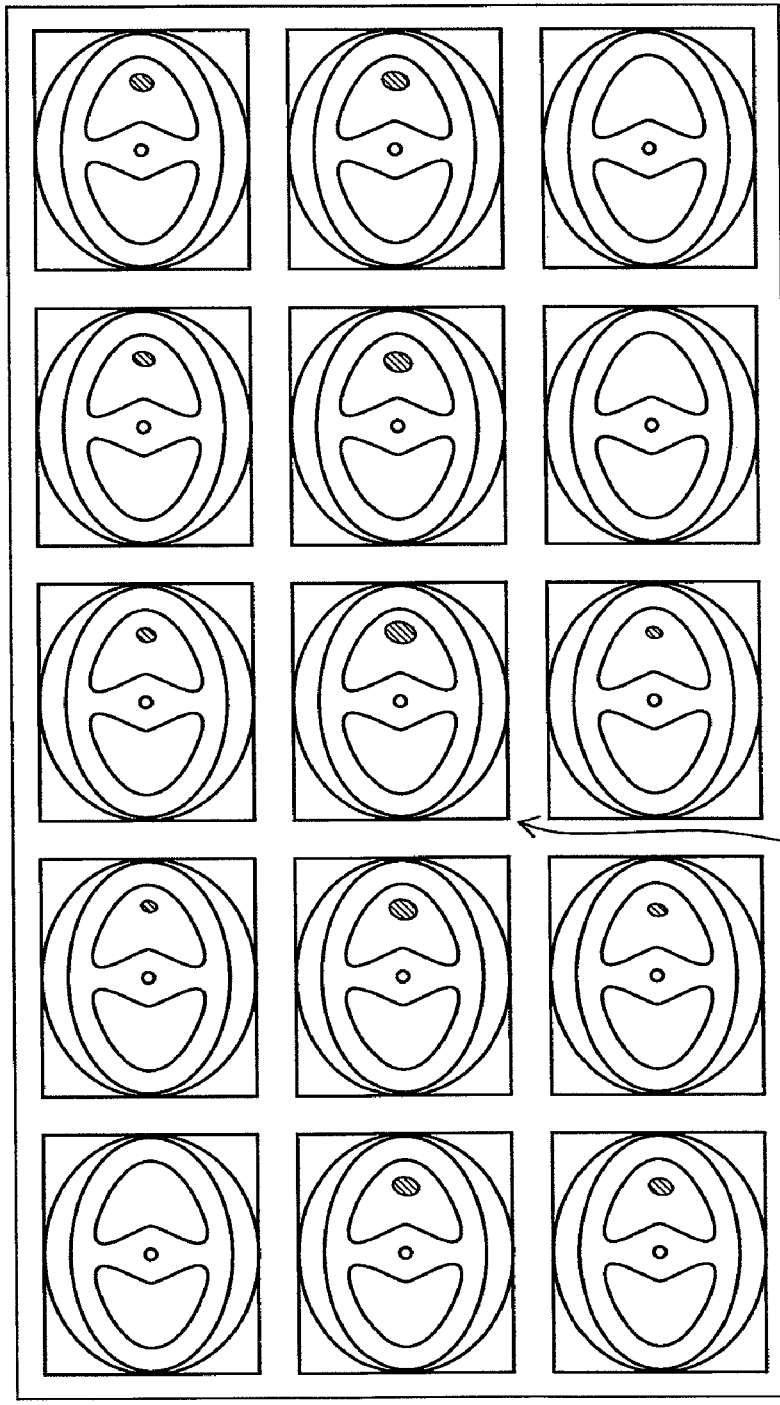
FIG. 11 is an imagery diagram of a monitor screen in which multi-display of a plurality of slice images including an abnormal shadow region is provided on a 15-split screen.

In other words, as shown in FIG. 11, using the slice image having the largest area of the abnormal shadow region as a reference slice image, an adjustment is made so that this reference slice image is arranged in the center (2, 3) of the 15-split screen.

The diagnostic radiologist can observe, on one screen, a plurality of slice images in which the images of the abnormal shadow region successively exist, and in which the slice image having the largest area of the abnormal shadow region is arranged in the center of the screen as shown in FIG. 11, thereby being able to easily recognize the size, shape, density change, etc., of the abnormal shadow region.

Also, if the number of slice images including the abnormal shadow region exceeds 15, the diagnostic radiologist can switch display screens or scroll the slice images by operating the keyboard 32 and/or the mouse 34. Furthermore, by performing an operation to zoom the slice images, simultaneous zoom display of all the images that are displayed in multi-screen mode can be provided, and also the images can be moved so that the zoomed abnormal shadow regions come to the centers of the respective screen segments.

If the number of slice images including the abnormal shadow region is smaller 15 and slice images not including the abnormal shadow region are also displayed, it is preferable that they are displayed, for example, with their display frames changed to different ones so that both slice images can easily be distinguished.

<Second Embodiment>

Figure 12:
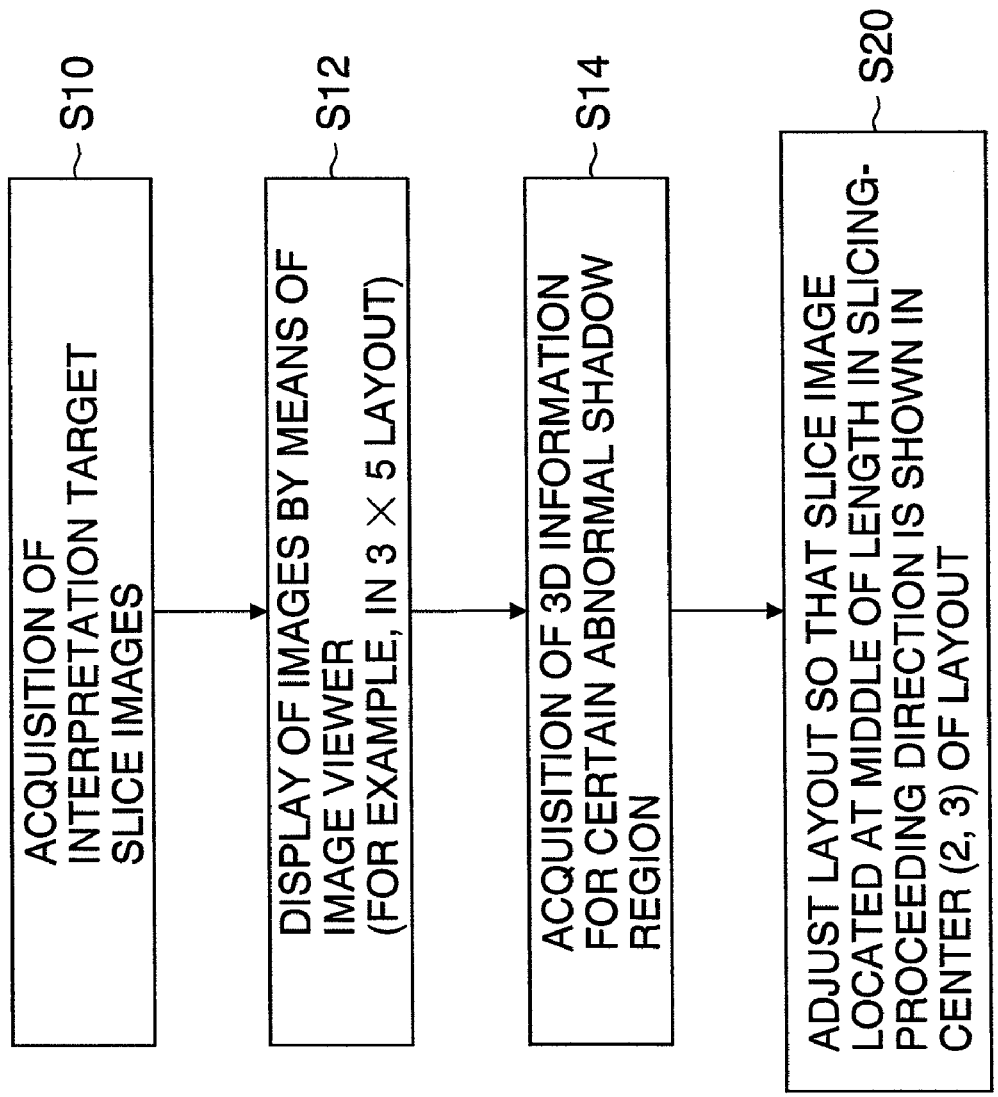
FIG. 12 is a flowchart illustrating a second embodiment of a medical image display method according to the present invention.

FIG. 12 is a flowchart illustrating a second embodiment of a medical image display method according to the present invention. Steps that are common to those in the first embodiment shown in FIG. 4 are provided with the same step numerals, and the detailed description thereof will be omitted.

Upon acquisition of 3D information representing the outer shape of an abnormal shadow region by means of step S14, based on this 3D information, a slice image in the center position of a plurality of slice images including the abnormal shadow region (slice image at the middle of the length in the slicing-proceeding direction (z-axis direction) of the abnormal shadow region) is obtained.

Then, with reference to the slice image at the middle of the length in the slicing-proceeding direction of the abnormal shadow region, the layout of the plurality of slice images including the abnormal shadow region on the split screen is determined, and a display screen for providing multi-screen display of the plurality of slice images including the abnormal shadow is created (step S20).

In other words, using the slice image at the middle of the length in the slicing-proceeding direction of the abnormal shadow region as a reference slice image, an adjustment is made so that this reference slice image is arranged in the center (2, 3) of the 15-split screen.

In the first embodiment, since an adjustment is made so that the slice image having the largest area of the abnormal shadow region is arranged in the center (2, 3) of the 15-split screen, for example, where the slice image having the largest area of the abnormal shadow region is located at a position corresponding to an end portion of the abnormal shadow region, the number of displayed slice images having the abnormal shadow region may be decreased, but in the second embodiment, since an adjustment is made so that the slice image at the middle of the length in the slicing-proceeding direction of the abnormal shadow region is arranged in the center (2, 3) of the 15-split screen, multi-display of more slice images having the abnormal shadow region can be provided on the 15-split screen.

<Third Embodiment>

Figure 13:
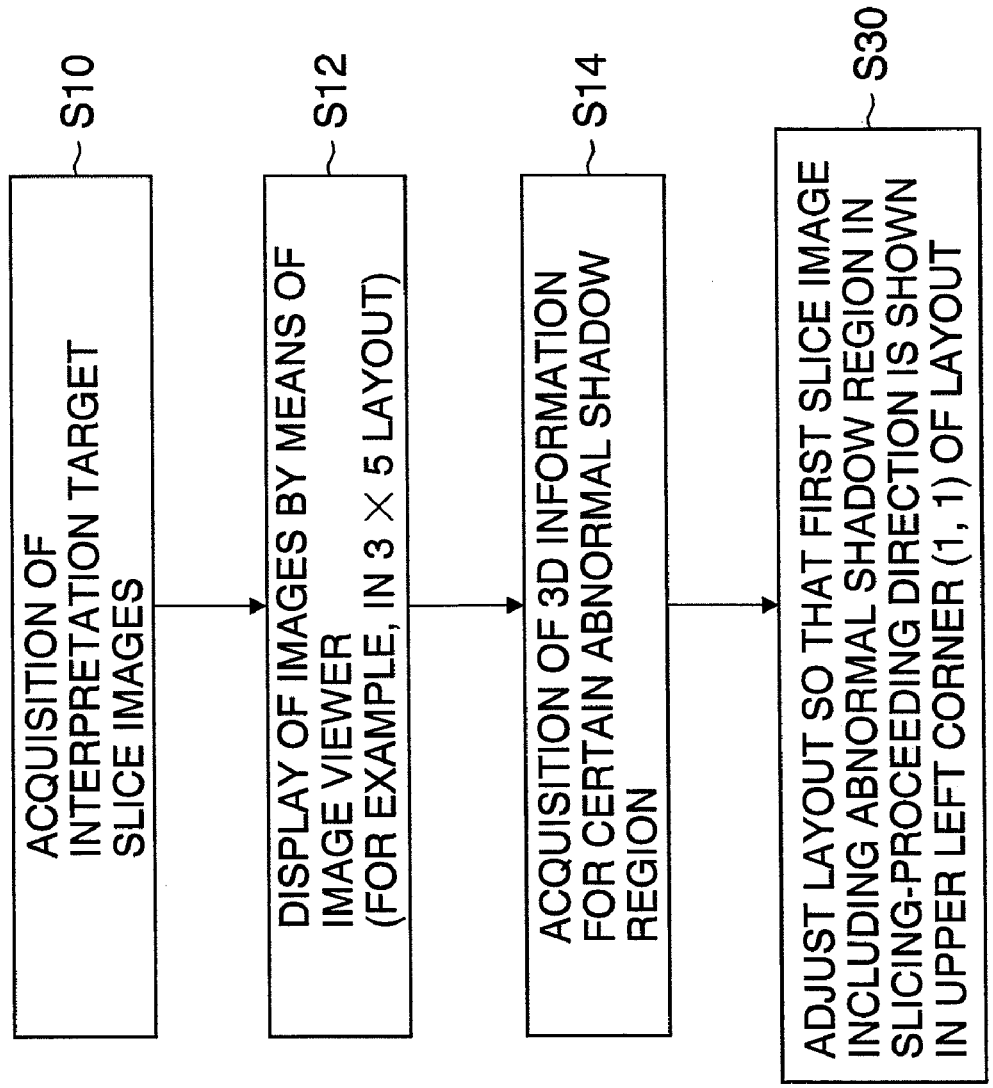
FIG. 13 is a flowchart illustrating a third embodiment of a medical image display method according to the present invention.

FIG. 13 is a flowchart illustrating a third embodiment of a medical image display method according to the present invention. Steps that are common to those in the first embodiment shown in FIG. 4 are provided the same step numerals, and the detailed description thereof will be omitted.

Upon acquisition of 3D information representing the outer shape of an abnormal shadow region by means of step S14, the first slice image in a plurality of slice images including the abnormal shadow region is obtained based on this 3D information. For example, a slice image with a smallest positional value in the slicing-proceeding direction (z coordinate) in the plurality of slice images including the abnormal shadow region is obtained, or since the slice images are provided with slice numbers for respective slicing positions in the z-axis direction, a slice image provided with the smallest slice number in the plurality of slice images including the abnormal shadow region abnormal shadow region is obtained.

Then, using the first slice image in the plurality of slice images including the abnormal shadow region as a reference slice image, the layout of the plurality of slice images including the abnormal shadow region on the split screen is determined, and a display screen for providing multi-screen display of the plurality of slice images including the abnormal shadow region is created (step S30).

In other words, using the first slice image in the plurality of slice images including the abnormal shadow region as a reference slice image, an adjustment is made so that this reference slice image is arranged in the upper left corner (1, 1) of the 15-split screen.

According to the third embodiment, as in the second embodiment, multi-display of more slice images having the abnormal shadow region can be provided on the 15-split screen, and also where there is a large number of slice images having an abnormal shadow region and the slice images are not displayed on one screen, the screen may be switched to the next page or the slice images may also be scrolled in the frame advance direction.

<Fourth Embodiment>

FIG. 14 is a flowchart illustrating a fourth embodiment of a medical image display method according to the present invention. Steps that are common to those in the first embodiment shown in FIG. 4 are provided the same step numerals, and the detailed description thereof will be omitted.

Upon acquisition of 3D information representing the outer shape of an abnormal shadow region by means of step S14, the number of a plurality of slice images including the abnormal shadow region is calculated based on this 3D information (step S40). For example, by adding 1 to the difference between the slice number of the slice image having the largest z-coordinate in the 3D information representing the outer shape of the abnormal shadow region, and the slice number of the slice image having the smallest z-coordinate, the number of the plurality of slice images including the abnormal shadow region can be calculated. Also by dividing the length in the slicing-proceeding direction of the abnormal shadow region by the interval of slicing for the slice images, the number of the plurality of slice images including the abnormal shadow region can be calculated.

Next, based on the thus-calculated number of the plurality of slice images including the abnormal shadow region and according to predetermined rules, a split screen having the number of screen segments corresponding to the number of slice images is determined. Then, where the determined split screen is different from the 15-split screen with a [3×5] matrix set at step S12, the screen is changed to the determined split screen (step S42).

For example, where the number of the plurality of slice images including the abnormal shadow region is six, the screen is changed to a six-split screen with a [2×3] matrix; where the number of the plurality of slice images including the abnormal shadow region is 14, the 15-split screen with a [3×5] matrix is used as it is; and where the number of the plurality of slice images including the abnormal shadow region is 20, the screen is changed to a 20-split screen with a [4×5] matrix.

In other word, based on the number of the plurality of slice images including the abnormal shadow region, determination is made to use a split screen having the smallest number of screen segments in split screens having the number of screen segments equal to or larger than the number of slice images.

This makes it possible to display the plurality of slice images including the abnormal shadow region as large as possible on one screen.

Also, where there is a large number of slice images including the abnormal shadow region, it becomes impossible to arrange all the images of the abnormal shadow region within one screen. In that case, determination is made to use a split screen with the largest number of screen segments. The split screen with the largest number of screen segments may be set according to the screen size of the monitor or by a user.

<Modification>

Although the first to third embodiments have referred to the case where a 15-split screen with a [3×5] matrix is set in advance, the present invention is not limited to this case, and a user may arbitrarily set or change split screen types (split screens having different numbers of screen segments in which one screen is divided laterally and longitudinally) as necessary. Also, the fourth embodiment may be applied to the first to third embodiments so that the screen is automatically set to be a split screen having the number of screen segments determined in the fourth embodiment.

Also, although these embodiments have referred to the case where a series of slice images taken by the X-ray CT apparatus 50 or the MRI apparatus 52 is the interpretation target, the present invention is not limited to this case, and a series of slice images acquired by other modalities such as Positron Emission Tomography (PET) apparatuses and Single Photon Emission Computed Tomography (SPECT) apparatuses, and fusion images of PET images and CT images can also be interpretation targets.

The method for determining the reference slice image based on 3D information representing the outer shape of the abnormal shadow region is also not limited to those in the embodiments, and it is possible, for example, to measure the position of the gravity center of the abnormal shadow region and determine the slice image closest to this gravity center position as a reference slice image to change the layout on the split screen.

Furthermore, the present invention is not limited to the case where the series of slice images is acquired from the in-house image DB 60 via the network 70 such as an in-house LAN, it may be acquired from an external database via a secure external network such as IPSec or SSL-VPN.

What is claimed is:

1. A medical image display apparatus comprising:
    an acquisition device which acquires a series of slice images constituting a three-dimensional medical image that is a diagnosis target;
    an abnormal shadow region acquisition device which acquires three-dimensional information for an abnormal shadow region included in the acquired series of slice images;
    a determination device which determines a display mode to provide multi-screen display of a plurality of slice images including the abnormal shadow region from the series of slice images based on the acquired three-dimensional information for the abnormal shadow region;
    a display screen creation device which creates a display screen for providing multi-screen display of the plurality of slice images including the abnormal shadow region based on the plurality of slice images including the abnormal shadow region and information for the determined display mode;
    an output device which outputs the created display screen to a display device;
    wherein the display screen creation device which provides the multi-screen for the plurality of slice images including the abnormal shadow region from the series of slice images further includes changing an order of display of the plurality of slice images automatically in an adjusted sequence of plurality of images slices including the abnormal shadow region based on abnormal shadow region information.

2. The medical image display apparatus according to claim 1, wherein the abnormal shadow region acquisition device includes: an extraction device which automatically extracts the abnormal shadow region included in the respective sliced images by analyzing the acquired series of slice images; and an outer shape information acquisition device which acquires three-dimensional information representing the outer shape of the extracted abnormal shadow region.

3. The medical image display apparatus according to claim 2, further comprising a recording device which records, in a recording medium, the three-dimensional information representing the outer shape of the abnormal shadow region acquired by the outer shape information acquisition device in association with the series of slice images, wherein
    the abnormal shadow region acquisition device acquires three-dimensional information for the abnormal shadow region by reading the three-dimensional information representing the outer shape of the abnormal shadow region recorded in the recording medium.

4. The medical image display apparatus according to claim 3, wherein:
    the information for the display mode includes information for specifying a split screen type from a plurality of split screen types having different numbers of screen segments, and information representing layout of the plurality of slice images including the abnormal shadow region on the split screen; and
    the determination device calculates the number of the plurality of slice images including the abnormal shadow region based on the acquired three-dimensional information for the abnormal shadow region, and determines, based on the calculated number of slice images, a split screen having the number of screen segments corresponding to the number of slice images.

5. The medical image display apparatus according to claim 4, wherein:
    the information for the display mode includes information for specifying a split screen type from a plurality of split screen types having different numbers of screen segments, and information representing layout of the plurality of slice images including the abnormal shadow region on the split screen; and
    the determination device determines the layout of the plurality of slice images including the abnormal shadow region on the split screen so that a slice image having a largest area of the abnormal shadow region in the plurality of slice images including the abnormal shadow region is arranged in the center of the display screen.

6. The medical image display apparatus according to claim 4, wherein:
    the information for the display mode includes information for specifying a split screen type from a plurality of split screen types having different numbers of screen segments, and information representing layout of the plurality of slice images including the abnormal shadow region on the split screen; and
    the determination device determines the layout of the plurality of slice images including the abnormal shadow region on the split screen so that a slice image at a center position in the plurality of slice images including the abnormal shadow region is arranged in a center of the display screen.

7. The medical image display apparatus according to claim 4, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a first slice image in the plurality of slice images including the abnormal shadow region is arranged in a corner of the display screen.

8. The medical image display apparatus according to claim 1, wherein the abnormal shadow region acquisition device includes: a display device which displays at least one slice image from the acquired series of slice images; a designation device which designates a seed point in the abnormal shadow region in the slice image displayed on the display device; an extraction device which extracts the abnormal shadow region with reference to the designated seed point; and an outer shape information acquisition device which acquires three-dimensional information for an outer shape of the extracted abnormal shadow region.

9. The medical image display apparatus according to claim 8, further comprising a recording device which records, in a recording medium, the three-dimensional information representing the outer shape of the abnormal shadow region acquired by the outer shape information acquisition device in association with the series of slice images, wherein
the abnormal shadow region acquisition device acquires three-dimensional information for the abnormal shadow region by reading the three-dimensional information representing the outer shape of the abnormal shadow region recorded in the recording medium.

10. The medical image display apparatus according to claim 9, wherein:
the information for the display mode includes information for specifying a split screen type from a plurality of split screen types having different numbers of screen segments, and information representing layout of the plurality of slice images including the abnormal shadow region on the split screen; and
the determination device calculates the number of the plurality of slice images including the abnormal shadow region based on the acquired three-dimensional information for the abnormal shadow region, and determines, based on the calculated number of slice images, a split screen having the number of screen segments corresponding to the number of slice images.

11. The medical image display apparatus according to claim 10, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a slice image having a largest area of the abnormal shadow region in the plurality of slice images including the abnormal shadow region is arranged in the center of the display screen.

12. The medical image display apparatus according to claim 10, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a slice image at a center position in the plurality of slice images including the abnormal shadow region is arranged in a center of the display screen.

13. The medical image display apparatus according to claim 10, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a first slice image in the plurality of slice images including the abnormal shadow region is arranged in a corner of the display screen.

14. The medical image display apparatus according to claim 1, wherein:
the information for the display mode includes information for specifying a split screen type from a plurality of split screen types having different numbers of screen segments, and information representing layout of the plurality of slice images including the abnormal shadow region on the split screen; and
the determination device calculates the number of the plurality of slice images including the abnormal shadow region based on the acquired three-dimensional information for the abnormal shadow region, and determines, based on the calculated number of slice images, a split screen having the number of screen segments corresponding to the number of slice images.

15. The medical image display apparatus according to claim 1, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a slice image having a largest area of the abnormal shadow region in the plurality of slice images including the abnormal shadow region is arranged in the center of the display screen.

16. The medical image display apparatus according to claim 1, wherein:
the information for the display mode includes information for specifying a split screen type from a plurality of split screen types having different numbers of screen segments, and information representing layout of the plurality of slice images including the abnormal shadow region on the split screen; and
the determination device determines the layout of the plurality of slice images including the abnormal shadow region on the split screen so that a slice image at a center position in the plurality of slice images including the abnormal shadow region is arranged in a center of the display screen.

17. The medical image display apparatus according to claim 1, wherein:
the information for the display mode includes information for specifying a split screen type from a plurality of split screen types having different numbers of screen segments, and information representing layout of the plurality of slice images including the abnormal shadow region on the split screen; and the determination device determines the layout of the plurality of slice images including the abnormal shadow region on the split screen so that a first slice image in the plurality of slice images including the abnormal shadow region is arranged in a corner of the display screen.

18. The medical image display apparatus of claim 1, displaying the plurality of slice images including the abnormal shadow region comprises using a second multi screen display of display form different from a first multi screen display and using a predetermined number of split screens based on the three-dimension information of the abnormal shadow region after the series of slice images obtained from the image acquisition device are displayed by the first multi screen display.

19. The medical image display apparatus of claim 1, wherein the determination device determines a slice image with the largest abnormal shadow region from among the plurality of successive slice images including the abnormal shadow region based on the three-dimension information of the obtained abnormal shadow region, and adjusts the layout of a plurality of the slice images including the abnormal shadow region so that slice image with the largest abnormal shadow region is located in the center of the layout of split screens in the multi screen display.

20. The medical image display apparatus of claim 1, wherein the determination device determines the slice image at the center position out from the plurality of slice images including the abnormal shadow region based on three-dimension information of the obtained abnormal shadow region, and adjusts the layout of a plurality of slice images including the abnormal shadow region so that the slice image at the center position gets located in the center of the layout of the split screens in the multi screen display.

21. The medical image display apparatus of claim 1, wherein the determination device determines first slice image among the plurality of successive slice images including the abnormal shadow region based on the obtained three-dimension information of the abnormal shadow region, and adjusts layout of a plurality of slice images including the abnormal shadow region so that the first slice image gets located at a corner of the layout of the split screens in the multi screen display.

22. The medical image display apparatus of claim 1, wherein the determination device calculates the number of plurality of slice images including the abnormal shadow region based on a three-dimension information of the obtained abnormal shadow region, and changes into a layout of split screens having a number of split screens corresponding to the number of slice images based on the calculated number of slice images.

23. The medical image display apparatus of claim 1, wherein slice images without abnormal shadow region are displayed at the same time as the plurality of slice images with the abnormal shadow region in case a number of the plurality of slice images including the abnormal shadow region is less than the number of split screens of the multi screen display and, slice images including abnormal shadow region are displayed to be distinguished from images without abnormal shadow region.

24. A medical image display method for a medical image display apparatus comprising the steps of:
acquiring a series of slice images constituting a three-dimensional medical image that is a diagnosis target;
acquiring three-dimensional information for an abnormal shadow region included in the acquired series of slice images;
determining a display mode to provide multi-screen display of a plurality of slice images including the abnormal shadow region from the series of slice images based on the acquired three-dimensional information for the abnormal shadow region;
creating a display screen for providing multi-screen display of the plurality of slice images including the abnormal shadow region based on the plurality of slice images including the abnormal shadow region and information for the determined display mode;
outputting the created display screen to a display device;
wherein the display screen creating provides the multi-screen for the plurality of slice images including the abnormal shadow region from the series of slice images and further includes changing an order of display of the plurality of slice images automatically in an adjusted sequence of plurality of images slices including the abnormal shadow region based on abnormal shadow region information.

25. A non-transitory tangible recording media in which computer readable code of the medical image display program causes a computer to execute:
acquiring a series of slice images constituting a three-dimensional medical image that is a diagnosis target;
acquiring three-dimensional information for an abnormal shadow region included in the acquired series of slice images;
determining a display mode to provide multi-screen display of a plurality of slice images including the abnormal shadow region from the series of slice images based on the acquired three-dimensional information for the abnormal shadow region;
creating a display screen for providing multi-screen display of the plurality of slice images including the abnormal shadow region based on the plurality of slice images including the abnormal shadow region and information for the determined display mode; and
wherein the display screen creation provides the multi-screen for the plurality of slice images including the abnormal shadow region from the series of slice images and further includes changing an order of display of the plurality of slice images automatically in an adjusted sequence of plurality of images slices including the abnormal shadow region based on abnormal shadow region information.

* * * * *